| United States Patent [19] | [11] Patent Number: 4,798,834 |
| Merritt et al. | [45] Date of Patent: Jan. 17, 1989 |

[54] OPTIONALLY SUBSTITUTED (3β-9,10-DIDEHYDRO-2,3-DIHYDRO ERGOLINE AS SEROTONERGIC FUNCTION ENHANCEMENT

[75] Inventors: Leander Merritt; John S. Ward, both of Indianapolis, Ind.

[73] Assignee: Eli Lilly and Company, Indianapolis, Ind.

[21] Appl. No.: 91,462

[22] Filed: Aug. 31, 1987

[51] Int. Cl.$^4$ ............... A61K 31/48; C07D 457/00
[52] U.S. Cl. ................................ 514/288; 546/67; 546/69
[58] Field of Search ............... 546/67, 69; 514/288

[56] References Cited

U.S. PATENT DOCUMENTS

| 3,113,133 | 12/1963 | Hoffman et al. | 546/69 |
| 3,580,916 | 5/1971 | Garbrecht | 546/69 |
| 3,992,385 | 11/1976 | Bach et al. | 546/67 |
| 4,166,182 | 8/1979 | Kornfeld | 546/67 |
| 4,201,862 | 5/1980 | Kornfeld | 546/67 |
| 4,348,391 | 9/1982 | Stütz et al. | 546/68 |

FOREIGN PATENT DOCUMENTS

| 2509471 | 9/1975 | Fed. Rep. of Germany | 546/67 |
| 2601473 | 7/1976 | Fed. Rep. of Germany | 546/67 |
| 3411981 | 10/1985 | Fed. Rep. of Germany | . |
| 3445784 | 6/1986 | Fed. Rep. of Germany | . |
| 1596210 | 8/1981 | United Kingdom | . |
| 2125041 | 2/1984 | United Kingdom | 546/67 |

OTHER PUBLICATIONS

Nakahara et al., Chem. Pharm. Bull. 25 (7), 1756–1763 (1977).
Sauer et al., CA 105–43137d.
Goodman et al., The Pharmaceutical Basis of Therapeutics 7th edition, pp. 247–256, pp. 628–635.
Kiguchi et al., "Total Synthesis of Ergot Alkaloid (±) Fumigaclavine B", *Heterocycles* 23 (8), 1925–1928 (1985).
Ninomiya et al., "Dehydrogenation with Phenylseleninic Anhydride in the Total Synthesis of Ergot Alkaloids", *Tetrahedron Letters*, 26, No. 35, 4187–4190 (1985).

*Primary Examiner*—Donald G. Daus
*Assistant Examiner*—Cecilia Shen
*Attorney, Agent, or Firm*—Edward P. Gray; Leroy Whitaker

[57] ABSTRACT

A therapeutic method employing 2,3-dihydroergolines is disclosed. Said method enhances serotonergic function in the nervous system of a mammal in need thereof, thereby finding application in serotonin-mediated physiological manifestations including memory, depression, anxiety, pain and appetite. Also disclosed are pharmaceutical compositions containing said 2,3-dihydroergolines in admixture with pharmaceutically acceptable diluents and carriers.

27 Claims, No Drawings

OPTIONALLY SUBSTITUTED (3β-9,10-DIDEHYDRO-2,3-DIHYDRO ERGOLINE AS SEROTONERGIC FUNCTION ENHANCEMENT

BACKGROUND OF THE INVENTION

Many naturally occurring and synthetic ergolines are known to bind to receptors for the neurotransmitters dopamine, noradrenalin and serotonin and to act as agonists or antagonists at said receptors. Given the breadth of this potential physiological activity, a central challenge lies in the development of therapeutically useful compounds that are sufficiently selective for a single neurotransmitter thus eliminating or reducing unwanted side effects during therapy. For example, this challenge has been met with the introduction of the selective serotonin antagonists methysergide and metergoline for the treatment of migraine and, in more recent years, the dopamine agonists bromocriptine and lisuride for the treatment of Parkinson's disease and hyperprolactinemia. Specifically with respect to serotonin (also known as 5-hydroxytryptamine or 5-HT), the receptors therefor have been divided into two major subtypes, 5-HT$_1$ and 5-HT$_2$, based on their relative affinities for [$^3$H]serotonin and [$^3$H]spiperone, respectively. The present invention discloses therapeutic methods utilizing certain 2,3-dihydroergolines which exhibit selectivity for serotonin receptors of the 5-HT$_1$ subtype and little or no affinity for the 5-HT$_2$ subtype, dopaminergic or adrenergic receptors. Said 2,3-dihydroergolines act as serotonin agonists thereby manifesting their physiological effects by an increase in endogenous serotonin activity.

DESCRIPTION OF PERTINENT ART

German Offenlegungsschrift 3411981 discloses the preparation of certain 2,3-dihydroergoline compounds by the reduction of the corresponding 2-bromoergolines with sodium borohydride in trifluoroacetic acid. The reduced species are said to be biologically active or are intermediates for compounds with biological activity in the central nervous system. In *Heterocycles* 23 (8) 1925–1928 (1985) is described the compound 2,3-dihydroisolysergine which is used as an intermediate in the synthesis of isolysergine. No utility is ascribed to any of the compounds disclosed therein. German Offenlegungsschrift 3445784 teaches various 2,3-dihydrolysergines as intermediates for the production of the biologically active 2,3-didehydro-analogs. The intermediate may be substituted at both the 6 and 8-position with (among others) methyl and with the 8-position substituent in either an α- or β-orientation. No utility is disclosed for the intermediate. British Patent Specification No. 1,596,210 discloses certain N-(2,3,β-dihydro-9-ergolen-8β-ylmethyl) ureas as being anti-hypertensive agents. Finally, certain ergolines exhibiting activity as serotonin antagonists are disclosed in U.S. Pat. No. 3,580,916 (lysergic acid and 9,10-dihydrolysergic acid esters) and U.S. Pat. No. 3,113,133 (indole nitrogen-substituted ergolines). None of the above references disclose or suggest that the 2,3-dihydrolysergine compounds used in the present invention would exhibit serotonin agonist activity and have the specific affinity for the 5-HT$_1$ receptor described hereinafter.

SUMMARY OF THE INVENTION

The present invention is directed to a method of enhancing serotonergic function in the nervous system of a mammal in need thereof. Said method comprises administering to said mammal a therapeutically effective amount of a compound of the formula:

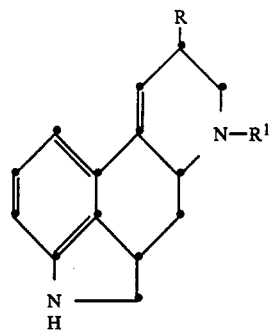

wherein R is methyl, hydroxymethyl, methylene, methylthiomethyl, phenylthiomethyl, pyridylthiomethyl, cyanomethyl and methoxycarbonyl; and R$^1$ is methyl, ethyl or n-propyl. Also disclosed are pharmaceutical compositions containing a therapeutically effective amount of one or more compounds useful in the present method in admixture with pharmaceutically acceptable diluents and carriers.

DETAILED DESCRIPTION OF THE INVENTION

The coumpounds used in the method of the present invention wherein R$^1$ is methyl are readily prepared by selectively reducing the 2,3-position of the corresponding ergoline to the 2,3-dihydro species. Any process for the reduction of a 2,3-double bond in an ergot alkaloid may be employed such as reduction by sodium borohydride, or triethylsilane in a suitable acidic soleent such as trifluoroacetic acid, hydrochloric acid, acetic acid, sulfuric acid and the like or mixtures thereof. Preferably the reduction is achieved utilizing triethylsilane in trifluoroacetic acid under reaction conditions sufficient to effect reduction to the 2,3-dihydroergoline. For those compounds wherein R$^1$ is ethyl or n-propyl, preparation is achieved by N-demethylation of the corresponding ergoline with cyanogen bromide followed by realkylation at the 6-position with, for example, the appropriate alkyl halide. The realkylated product is then reduced as described above. The reaction conditions for the reducbtion are conventional in the art and are readily within the skill of the artisan. Similarly, the precursor ergolines are well known in the art and may be prepared by conventional techniques. See, for example: Spilsbury et al., *J. Chem. Soc.* 1961, 2085; Schreier, *Helv. Chim. Acta* 1958, 41, 1984; Stoll et al., *Helv. Chim. Acta* 1949, 32, 1949; Nakahara et al., *Chem. Phar. Bull. Japan* 1977, 25, 1756; Semonsky et al., *Coll. Czech. Chem. Comm.* 1968, 33, 577; Kornfeld et al., U.S. Pat. No. 3,901,894; Troxler et al., *Helv. Chim. Acta* 1968, 51, 1060; and Stutz et al., *J. Med. Chem.* 1978, 21, 754; each of which is incorporated herein by reference as are all other references cited herein.

Of the compounds which may be utilized in the method and compositions of the present invention those compounds which are in the β-configuration at the 8-position of the molecule are preferred. Of the preferred compounds which may be utilized in the present invention, those compounds wherein R$^1$ is methyl are particularly preferred. Of the particularly preferred compounds for use in the method and compositions of the present invention, the compound (3β)-2,3-dihydrolysergine is most particularly preferred.

The 2,3-dihydroergolines useful in the method of the present invention act as serotonin agonists and may be used therapeutically to enhance serotonergic function in a mammal in need thereof. Serotonin agonists, monoamine oxidase inhibitors and serotonin uptake inhibitors (each of which enhance serotonergic function) have been shown to affect neurally mediated functions in mammals such as, for example, memory, depression, anxiety, pain and appetite. See, for example, Glennon, *J. Med. Chem.* 1987, 30, 1; Stahl et al., *Trends Pharm. Sci.* 1986, 349; Dourish et al., *Trends Pharm. Sci.* 1986, 212; Fuller, *J. Clin. Psychiatry* 1986, 47:4 (*Suppl*), 4; and Wong et al. *J. Neural Transmission*, 1985, 64, 251. Accordingly, the method claimed herein finds application in various therapeutic modalities including anti-depressive therapy, analgesia, anti-anxiety therapy and the like. Use in anti-depressive therapy is preferred. Of course once the skilled artisan becomes aware of additional physiological functions mediated by enhanced serotonin function, additional therapies will become self-evident. It is contemplated that such therapies will be encompassed by the method claimed herein.

To enhance serotonergic function per the claimed method, a therapeutically effective amount of one or more of the compounds of formula I are administered. By "therapeutically effective" is meant that amount of one or more of the compounds of formula I sufficient to effect the enhanced serotonergic function (and the physiological function mediated thereby) in the mammal being treated. The skilled artisan will readily appreciate that the therapeutically effective amount used in the present method may vary widely particularly where the route of administration and the particular compound to be employed are considerations. Of course other factors such as the weight of the mammal as well as the time, frequency and pharmaceutical formulation employed in the administration are to be considered in determining the therapeutically effective dose in a given situation. Suffice it to say that the precise therapeutically effective dose to be administered in a particular instance can be readily ascertained by the skilled artisan utilizing conventional dose titration techniques. Typically, though not necessarily, such therapeutically effective dosage amounts may range anywhere from about 0.001 milligram (mg) per kilogram (kg) of body weight per day to about 50 mg per kg of body weight per day.

In carrying out the method of the present invention, one or more of the compounds of formula I is administered internally in the form of a pharmaceutical composition comprising said compound(s) in admixture with one or more pharmaceutically-acceptable non-toxic diluents or carriers, i.e., a diluent or carrier which is chemically inert to the compound to be administered and which has no detrimental side effects or toxicity under the conditions of use. Internal administration of the compounds may be parenteral as for example by intraperitoneal, subcutaneous or intravenous injection. Dosage forms for parenteral administration can be prepared by suspending or dissolving an amount of the compound in a non-toxic liquid vehicle suitable for injection such as an aqueous or oleaginous medium and sterilizing the suspension or solution. Alternatively, a measured amount of the compound may be placed in a vial and the vial and its contents sterilized and sealed. An accompanying vial or vehicle can be provided for purposes of mixing prior to administration. Pharmaceutical compositions adapted for parenteral administration employ diluents and carriers such as water and water-miscible organic solvents such as sesame oil, groundnut oil, aqueous propylene glycol and N,N'-dimethylformamide. Examples of such pharmaceutical compositions include sterile, isotonic, aqueous saline solutions of the compound which can be buffered with a pharmaceutically acceptable buffer and which are pyrogen free.

Internal administration of said compound(s) may also be accomplished by means of oral pharmaceutical dosage forms. These include any of the conventional solid or liquid dosage forms such as powders, tablets, capsules, suspensions, solutions, syrups and the like including any sustained release preparations of the above. Such oral pharmaceutical dosage forms employ pharmaceutically acceptable diluents and carriers, excipients, lubricants and the like such as glucose, lactose, sucrose, corn and potato starch, sodium carboxymethylcellulose, ethyl cellulose, cellulose acetate, powdered gum tragacanth, gelatin, alginic acid, agar, stearic acid, sodium, calcium and magnesium stearates, sodium lauryl sulfate, polyvinylpyrrolidone, sodium citrate, calcium carbonate, dicalcium phosphate; as well as various buffering agents, surfactants, emulsifiers, dispersing agents, flavoring agents and the like.

Preparation of the pharmaceutical compositions described herein may be readily achieved by one skilled in the art. Further, the skilled artisan will appreciate that the ultimate pharmaceutical composition may be provided in multiple or discrete, unit-dose fashion with the latter being preferred. Additional information pertinent to the compositions of the present invention may be obtained by reference to standard treatises such as *Remington's Pharmaceutical Sciences*, Seventeenth Edition, Mack Publishing Co., Easton, Pa. (1980).

The following examples are provided as a means of illustrating the present invention and are not to be construed as a limitation thereon. The preparation of certain of the compounds of formula I useful in the claimed method may be achieved as follows.

EXAMPLE 1

Preparation of (3β)-2,3-Dihydrolysergine

Lysergine was prepared by the method of Schreier, *Helv. Chim. Acta* 1958, 41, 1984. A mixture of 25 milliliters (ml) of trifluoroacetic acid (TFA) and 6.81 grams (g), i.e., 58.6 millimole (mmol) triethylsilane was vigorously stirred as 3.38 g (14.2 mmol) lysergine was added in portions. The resultant mildly exothermic reaction was stirred at ambient temperature for 16 hours. The solvent was evaporated in vacuo and the residue was dissolved in water and extracted with ether. The aqueous portion was retained and made basic with 5 normal (N) NaOH (pH greater than 10) and was extracted with three 200 ml portions of ether. The organic extracts were combined and were then dried over $Na_2SO_4$ and evaporated in vacuo to give a solid residue. The solid residue (2.36 g) was separated by high performance liquid chromatography (HPLC) using an 8 liter (l) gradient beginning with hexane:ethyl acetate:ammonium hydroxide (1:1:1%) and going to 100% ethyl acetate. Recrystallization of the recovered material from a mixture of ethyl acetate/hexane gave 1.66 g of the title compound, (49%) melting point (mp) 199°–201° centigrade (C), decomposition (dec.), $[\alpha]_{589nm}+18°$, $[\alpha]_{365nm}+239°$ (c=0.53 percent, pyridine).

Analysis ($C_{16}H_{20}N_2$): Calc: C, 79.96; H, 8.39; N, 11.66; Found: C, 80.11; H, 8.27; N, 11.57.

EXAMPLE 2

Preparation of (3β)-2,3-Dihydroisolysergine

Isolysergine was prepared by the method of Schreir, supra. Following procedures essentially as described in Example 1, a mixture of 12 ml of TFA, 3.27 g (28.1 mmol) triethylsilane and 1.62 g (6.8 mmol) of isolysergine was stirred overnight. Following work-up as described in Example 1 and recrystallization from pentane, 0.4 g of the title compound (24%) was recovered, mp. 85°–87° C., $[\alpha]_{589nm}+126°$, $[\alpha]_{365nm}+25°$ (c=0.54 percent, pyridine).

Analysis ($C_{16}H_{20}N_2$): Calc: C, 79.96; H, 8.39; N, 11.66; Found: C, 79.86; H, 8.44; N, 11.55.

EXAMPLE 3

Preparation of (3β)-2,3-Dihydrolysergol

Lysergol was prepared as described by Stoll et al., *Helv. Chim. Acta* 1949, 32, 1949. Following procedures essentially as described in Example 1, a mixture of 7 ml of TFA, 1.78 g (15.28 mmol) triethylsilane and 0.508 g (2.0 mmol) of lysergol was stirred for 3 hours and gave 0.13 g of the title compound (25%) following column chromatography (50 g silica gel, chloroform:methanol:ammonium hydroxide eluent, 8:2:0.5%), mp. 177°–178.5° C.

Analysis ($C_{16}H_{20}N_2O$): Calc: C, 74.97; H, 7.86; N, 10.93; Found: C, 74.68; H, 7.66; N, 10.81.

EXAMPLE 4

Preparation of (3β)-2,3-Dihydrolysergene

Lysergene was prepared as described by Nakahara et al., *Chem. Phar. Bull. Japan* 1977, 25, 1756. Following procedures essentially as described in Example 1, a mixture of 9 ml of TFA, 2.4 g (20.7 mmol) triethylsilane and 1.18 g (5.0 mmol) of lysergene provided 0.34 g of the title compound (28%) following HPLC and recrystallization from a mixture of diethyl ether/pentane, mp. 153°–155° C.

Analysis ($C_{16}H_{18}N_2 \cdot 0.25\ H_2O$): Calc: C, 79.14; H, 7.68; N, 11.57; Found: C, 78.76; H, 8.00; N, 11.57.

EXAMPLE 5

Preparation of (3β,5β,8β)-9,10-Didehydro-2,3-dihydro-6-methyl-8-(methylthiomethyl) ergoline (5β,8β)-9,10-didehydro-6-methyl-8-(methylthiomethyl)ergoline was prepared according to the method of Kornfeld et al. in U.S. Pat. No. 3,901,894. Following procedures essentially as described in Example 1, a mixture of 20 ml of TFA, 5.24 g (45.1 mmol) of triethylsilane and 3.1 g (10.9 mmol) of (5β,8β)-9,10-didehydro-6-methyl-8-(methylthiomethyl)ergoline was stirred for 5 hours and gave 1.34 g of the title compound (42%) after HPLC and recrystallization from a mixture of diethyl ether/hexane, mp. 93°–97° C.

Analysis ($C_{17}H_{22}N_2S \cdot 0.25\ H_2O$): Calc: C, 70.18; H, 7.79; N, 9.63; Found: C, 70.39; H, 7.40; N, 9.38

EXAMPLE 6

Preparation of (3β,5β,8β)-9,10-Didehydro-2,3-dihydro-6-methylergoline-8-acetonitrile (5β,8β)-9,10-didehydro-6-methylergoline-8-acetonitrile was prepared according to the method of Troxler et al., *Helv. Chim. Acta* 1968, 51, 1060. Following procedures essentially as described in Example 1, a mixture of 10 ml of TFA, 1.82 g (15.7 mmol) of triethylsilane and 1.0 g (3.8 mmol) of (5β,8β)-9,10-didehydro-6-methylergoline-8-acetonitrile was stirred overnight and gave 0.37 g of the title compound (37%) after recrystallization from a mixture of ethyl acetate/diethyl ether, mp. 180°–182° C., $[\alpha]_{589nm}+14°$ (c=0.46 percent, pyridine).

Analysis ($C_{17}H_{19}N_3$): Calc: C, 76.95; H, 7.22; N, 15.84; Found: C, 77.20; H, 7.22; N, 15.66.

EXAMPLE 7

Preparation of (3β,5β,8β)-9,10-Didehydro-2,3-dihydro-6-methyl-8-(phenylthiomethyl) ergoline (5β,8β)-9,10-didehydro-6-methyl-8-(phenylthiomethyl)ergoline was prepared as described by Kornfeld et al. supra. Following procedures essentially as described in Example 1, a mixture of 12 ml of TFA, 3.0 g (26.1 mmol) of triethylsilane and 2.32 g (6.7 mmol) of (5β,8β)-9,10-didehydro-6-methyl-8-(phenylthiomethyl)ergoline was stirred overnight and provided 0.81 g of the title compound (35%) following HPLC (5% methanol/methylene chloride), mp. 54°–58° C.

Analysis ($C_{22}H_{24}N_2S$): Calc: C, 75.82; H, 6.94; N, 8.04 Found: C. 75.99; H, 6.84; N, 8.11

EXAMPLE 8

Preparation of (3β,5β,8β)-9,10-Didehydro-2,3-dihydro-6-methyl-8-(2-pyridylthiomethyl)ergoline (5β,8β)-9,10-didehydro-6-methyl-8-(2-pyridylthiomethyl)ergoline was prepared as described by Stutz et al., *J. Med. Chem* 1978, 21, 754. Following procedures essentially as described in Example 1, a mixture of 12 ml of TFA, 2.9 g (25.0 mmol) of triethylsilane and 2.23 g (6.4 mmol) (5β,8β)-9,10-didehydro-6-methyl-8-(2pyridylthiomethyl)ergoline was stirred overnight and gave 0.85 g of the title compound (38%) following HPLC (5% methanol/chloroform/0.5% ammonium hydroxide) and recrystallization from diethyl ether/hexane, mp. 68°–71° C.

Analysis ($C_{21}H_{23}N_3S$): Calc: C, 72,17; H, 6.63; N, 12.02; Found: C, 72.41; H, 6.51; N, 12.21.

EXAMPLE 9

Preparation of (3β)-2,3-Dihydro-methyllysergate

Following procedures essentially as described in Example 1, a mixture of 13 ml of TFA, 3.4 g (29.3 mmol) of triethylsilane and 2.0 g (7.1 mmol) of methyllysergate was stirred overnight and gave 1.3 g of the title compound (66%) following recrystallization from a mixture of diethyl ether/hexane, mp. 80°–85° C.

Analysis ($C_{17}H_{20}N_2O_2$): Calc: C, 71.81; H, 7.09; N, 9.85; Found: C, 71.63; H, 6.85; N, 9.64.

EXAMPLE 10

Preparation of (3β,5β,8β)-9,10-Didehydro-2,3-dihydro-8-methyl-6-propylergoline A mixture of 1.5 g (6.7 mmol) of 6-desmethyllysergine (prepared by the N-demethylation of lysergine by cyanogen bromide), 1.8 g (13 mmol) of anhydrous potassium carbonate, 2.2 g (13 mmol) of 1-iodopropane and 50 ml of dry dimethylformamide was stirred for 42 hours. The solvent was evaporated in vacuo and the residue was digested with two 75 ml portions of ether and then filtered. The ether extracts were evaporated and the resulting solid residue was suspended in cold ether and collected by filtration to give 0.72 g (40%) of single spot material by thin layer chromatography (methanol:chloroform, 1:9). The NMR of the material was consistent with that expected for 6-propylergoline. Reduction was accomplished as described previously by stirring a mixture of 5 ml TFA, 1.3 g (11.1 mmol) of triethylsilane and 0.72 g (2.7 mmol) of 6-propyllysergine for 6 hours. The resultant was worked up as described above and gave 0.05 g of the title compound (7%) following HPLC and recrystallization from methanol/petane, mp. 135°–137° C.

Analysis ($C_{18}H_{24}N_2$): Calc: C, 80.55; H, 9.01: N, 10.44; Found: C, 80.75; H, 8.90; N, 10.33.

As noted previously, the compounds used in the present method exhibit electivity for serotonin receptors of the 5-$HT_1$ subtype with diminished affinity for the 5-$HT_2$ subtype. The relative affinities for the receptor subtypes was determined as follows.

Rat brain frontal cortex from male Wistar rats (140–160 g) was dissected, homogenized and prepared according to the method of Nelson et al., *Mol. Pharmacol.* 1978, 14, 983. The pellet from the frontal cortex homogenates was suspended in 0.05 molar (M) Tris buffer containing 10 micromolar (μM) pargyline and 4 millimolar (mM) $Ca^{++}$ to give a final protein concentration of 250–350 microgram (μg) per sample. The method of Bennett and Snyder (*Mol. Pharmacol.* 1976, 12, 373) was used for determining binding to 5-$HT_1$ sites using 2 nanomolar (nM) [$^3$H]serotonin as the radioactive ligand and 10 μM serotonin for nonspecific binding. The method of Peroutka and Snyder (*Mol. Pharmacol.* 1979, 16, 687) was used for determining binding to 5-$HT_2$ sites using 0.7–0.9 nM [$^3$H]spiperone as the radioactive ligand and 1 μM of lysergic acid diethylamide for nonspecific binding. All radioactive ligands were obtained from New England Nuclear, Boston, Mass., USA. Specific binding was determined as the difference between total binding and nonspecific binding. Eleven concentrations of each of the compounds tested were used between 0.1 and 10,000 nM. All samples were run in duplicate. Using the method of Munson and Rodbar (*Anal. Biochem.* 1980 107, 220), $IC_{50}$ values were determined as the amount of the compound tested which reduced the specific binding of the radioactive ligand by 50 percent. For serotonin, the $IC_{50}$ at 5-$HT_1$ and 5-$HT_2$ binding sites was 4 nM and 5,000 nM, respectively. For spiperone, the $IC_{50}$ so at 5-$HT_1$ and 5-$HT_2$ binding sites was 400 nM and 1.0 nM, respectively. The results of these binding studies are shown in Table I.

TABLE I

| Compound of Example No. | $IC_{50}$ (nM) 5-$HT_1$ Receptor | $IC_{50}$ (nM) 5-$HT_2$ Receptor | Selectivity Ratio[a] |
|---|---|---|---|
| 1 | 17 | 1665 | 100 |
| 2 | 20 | >1000 | NA[b] |
| 3 | 26 | 2650 | 102 |
| 4 | 80 | 3820 | 48 |
| 5 | 20 | 1330 | 66 |
| 6 | 20 | 2120 | 106 |
| 7 | 8 | 210 | 26 |
| 8 | 3 | 110 | 28 |
| 9 | 40 | 1620 | 40 |
| 10 | 240 | >1000 | NA |

[a]The Selectivity Ratio is the $IC_{50}$ 5-$HT_2$ $IC_{50}$ 5-$HT_1$ value. Values greater than 1 indicate selectivity for the 5-$HT_1$ receptor.
[b]NA means not assessable.

As can be readily seen from Table I, each of the compounds tested showed high affinity and selectivity for the 5-$HT_1$ receptor. Noteworthy are the compounds of Examples 1, 2, 3 and 6 which each had a Selectivity Ratio of at least 100 indicating at least a 100-fold preference for the 5-$HT_1$ receptor site.

The effect of certain of the compounds of formula I on concentrations of serotonin and the serotonin metabolite, 5-hydroxyindole acetic acid (5-HIAA) in rat brain as well as corticosterone concentrations in the serum of rats was determined as follows.

Male Wistar rate (HSD/[WI]BR) weighing about 150 g were kept in a temperature-controlled (24° C.) and light-controlled room (lights on from 7:00 A.M. to 7:00 P.M.) with food and water freely available. The compounds to be tested were dissolved in dilute hydrochloric acid and injected subcutaneously. Five rats per group were used in each experiment. The rats were decapitated one hour after injection and the brains were excised quickly, frozen on dry ice and stored at −15° C. before analysis. Serotonin and 5-HIAA concentrations were determined by liquid chromatography with electrochemical detection. See Fuller et al., *Biochem. Pharmacol.* 1977, 26, 2087 and Perry et al., *Soc. Neurosci. Abstr.* 1979, 5, 348. Serum corticosterone levels were determined spectrofluorometrically by the method of Solem et al., *Scand. J. Clin. Lab. Invest.* 1965, 17, suppl. 80, 1.

The compounds of examples 1–3, 5 and 6 were all found to increase the concentration of serotonin and decrease the concentration of 5-HIAA in the brain indicating that the compounds decrease serotonin turnover. Additionally, each of these compounds increased serum corticosterone concentrations. The minimum effective doses of these same compounds which produced a statistically significant decrease in 5-HIAA concentration and a statistically significant increase in serum corticosterone concentration are shown in Table II. The minimum effective dose is the lowest dose producing significant differences from a control group (p<0.05).

TABLE II

| Compound of Example No. | Minimum effective dose suppressing 5-HIAA[a] | Minimum effective dose increasing serum corticosterone[a] |
|---|---|---|
| 1 | 0.03 | 0.1 |
| 2 | 0.001 | 0.003 |
| 3 | 1 | 0.1 |
| 5 | 0.1 | 1 |
| 6 | 0.1 | 0.1 |

[a]In milligrams per kilogram (mg/kg), subcutaneous.

The compound of Example 1 was further studied to determine its ability to decrease the accumulation of the serotonin precursor, 5-hydroxytryptophan in rat hypothalamus. The protocol previously described for neurochemical determinations was repeated with the following modification. To each of the five rats in the treatment group was administered the amino acid decarboxylase inhibitor m-hydroxybenzylhydrazine (also known as NSD-1015). See Euvard et al., *Eur. J. Pharmacol.* 1980, 63, 65 and Hamon et al., *Arch. Pharmacol.* 1976, 294, 99. The NSD-1015 was administered at a dose of 100 mg/kg (intraperitoneal) 30 minutes before decapitation and 30 minutes after the dose of the test compound of Example 1 was given. The results are shown in Table III.

TABLE III

| Dose of Test Compound[a] | 5-Hydroxytryptophan Concentration in Hypothalamus[b] |
|---|---|
| 0 | 1.92 ± 0.07 |
| 0.01 | 1.64 ± 0.07[c] |
| 0.03 | 1.19 ± 0.05[c] |
| 0.1 | 0.73 ± 0.02[c] |
| 0.3 | 0.71 ± 0.02[c] |

[a]The subcutaneous dose of the compound of Example 1 in mg/kg.
[b]Expressed in nanomoles per gram. Mean values ± standard errors for five rats in each treated group and six rats in the control group.
[c]Significant decrease (p <0.01).

As can be seen from the data shown in Table III, the compound (3β)-2,3-dihydrolysergine (i.e., the compound of Example 1) produced a dose related decrease in 5-hydroxytryptophan accumulation in the hypothalamus of NSD-1015 treated rats. Significant effects were detected at all of the doses used with a maximal reduction of serotonin turnover observed at 0.1 mg/kg.

We claim:

1. A method of enhancing serotonergic function in the nervous system of a mammal in need thereof comprising administering to said mammal a therapeutically effective amount of a compound of the formula:

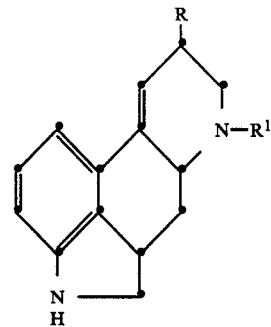

wherein R is methyl, hydroxymethyl, methylene, methylthiomethyl, phenylthiomethyl, pyridylthiomethyl, cyanomethyl and methoxycarbonyl; and R¹ is methyl, ethyl or n-propyl.

2. The method of claim 1 employing a compound wherein R¹ is methyl.

3. The method of claim 2 wherein said enhanced serotonergic function produces an anti-depressant effect in said mammal.

4. The method of claim 3 wherein the compound employed is (3β)-2,3-dihydrolysergine.

5. The method of claim 3 wherein the compound employed is (3β)-2,3-dihydroisolysergine..

6. The method of claim 3 wherein the compound employed is (3β)-2,3-dihydrolysergol.

7. The method of claim 3 wherein the compound employed is (3β)-2,3-dihydrolysergene.

8. The method of claim 3 wherein the compound employed is (3β,5β,8β)-9,10-didehydro-2,3-dihydro-6-methyl-8-(methylthiomethyl) ergoline.

9. The method of claim 3 wherein the compound employed is (3β,5β,8β)-9,10-didehydro-2,3-dihydro-6-methylergoline-8-acetonitrile.

10. The method of claim 3 wherein the compound employed is (3β,5β,8β)-9,10-didehydro-2,3-dihydro-6-methyl-8-(phenylthiomethyl) ergoline.

11. The method of claim 3 wherein the compound employed is (3β,5β,8β)-9,10-didehydro-2,3-dihydro-6-methyl-8-(2-pyridylthiomethyl) ergoline.

12. The method of claim 3 wherein the compound employed is (3β)-2,3-dihydro-methyllysergate.

13. The method of claim 3 wherein the compound employed is (3β,5β,8β)-9,10-didehydro-2,3-dihydro-8-methyl-6-propylergoline.

14. A pharmaceutical composition for enhancing serotonergic function in the nervous system comprising a therapeutically effective amount of a compound of the formula:

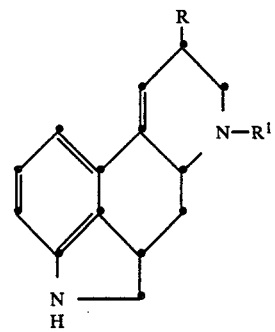

wherein R is methyl, hydroxymethyl, methylene, methylthiomethyl, phenylthiomethyl, pyridylthiomethyl, cyanomethyl, and methoxycarbonyl; and R¹ is methyl, ethyl, or n-propyl in admixture with pharmaceutically acceptable diluents and carriers.

15. The pharmaceutical composition of claim 14 employing a compound wherein R¹ is methyl.

16. The pharmaceutical composition of claim 15 in unit dose form.

17. The pharmaceutical composition of claim 15 wherein the compound employed is (3β)-2,3-dihydrolysergine.

18. The pharmaceutical composition of claim 15 wherein the compound employed is (3β)-2,3-dihydroisolysergine.

19. The pharmaceutical composition of claim 15 wherein the compound employed is (3β)-2,3-dihydrolysergol.

20. The pharmaceutical composition of claim 15 wherein the compound employed is (3β)-2,3-dihydrolysergene.

21. The pharmaceutical composition of claim 15 wherein the compound employed is (3β,5β,8β)-9,10-didehydro-2,3-dihydro-6-methyl-8-(methylthiomethyl) ergoline.

22. The pharmaceutical composition of claim 15 wherein the compound employed is (3β,5β,8β)-9,10-didehydro-2,3-dihydro-6-methylergoline-8-acetonitrile.

23. The pharmaceutical composition of claim 15 wherein the compound employed is (3β,5β,8β)-9,10- didehydro-2,3-dihydro-6-methyl-8-(phenylthiomethyl) ergoline.

24. The pharmaceutical composition of claim 15 wherein the compound employed is (3β,5β,8β)-9,10-didehydro-2,3-dihydro-6-methyl-8-(2-pyridylthiomethyl) ergoline.

25. The pharmaceutical composition of claim 15 wherein the compound employed is (3β)-2,3-dihydromethyllysergate.

26. The pharmaceutical composition of claim 15 wherein the compound employed is (3β,5β,8β)-9,10-didehydro-2,3-dihydro-8-methyl-6-propylergoline.

27. The compound (3β)-2,3-dihydrolysergine.

* * * * *